United States Patent [19]

Borchert

[11] 4,308,398

[45] Dec. 29, 1981

[54] ELIMINATION OF REDUCING SUGARS PRESENT IN TRISODIUM CITRATE

[75] Inventor: Peter J. Borchert, Elkhart, Ind.

[73] Assignee: Miles Laboratories, Inc., Elkhart, Ind.

[21] Appl. No.: 175,258

[22] Filed: Aug. 4, 1980

[51] Int. Cl.³ ............................................. C07C 59/265
[52] U.S. Cl. ..................................................... 562/584
[58] Field of Search ........................................... 562/584

[56] References Cited

U.S. PATENT DOCUMENTS 3,944,606  3/1976  Rieger et al. ..................... 562/584

Primary Examiner—Paul J. Killos

[57] ABSTRACT

A method of substantially depressing or eliminating reducing sugars present in trisodium citrate is disclosed. The method involves contacting the reducing sugars with a hydroxylamine under neutral or alkaline conditions.

4 Claims, No Drawings

ELIMINATION OF REDUCING SUGARS PRESENT IN TRISODIUM CITRATE

BACKGROUND OF THE INVENTION

Citric acid can be produced in commercial quantities by the fermentation of carbohydrate materials using various strains of citric acid-producing fungi. Certain strains of Aspergillus and Penicillium have proved to be useful, for example *Asperigullus niger; A. clavatus; A. wentiri; A. luchuensis; Penicillium citrinum;* and *P. luteum.*

One form of fermentation process employed in the art for citric acid production involves fermentation by *A. niger* in submerged culture. The fermentation substrate can be a carbohydrate material such as invert sugars, partially-refined sucrose sources, glucose and starch hydrolyzates obtained from highly refined starches. For example, corn starch can be hydrolyzed into sugars such as glucose by treatment with acids such as hydrochloric acid. Corn starch can also be enzymatically converted by alpha-amylase and amyloglucosidase into such sugars. After the starch is converted into sugar, the resulting sugar-containing material is subjected to the action of a citric-acid producing strain of a fungus in the presence of nutrients, under conditions conducive to fermentation, to produce citric acid.

During the hydrolysis of starch into sugars, by-products are formed, including reducing (reversion) sugars such as amino sugars, e.g., glucosamine; oligosaccharides, e.g., isomaltose and glucose. The major reducing sugar present apparently is glucose. These reducing sugars are carried over and are present in subsequent steps, including the production of citric acid, subsequent purification of citric acid and conversion of citric acid into trisodium citrate.

One major market for trisodium citrate is its use in detergents as a "builder". Some dyes present in commercially available detergents are susceptible to color fading in the presence of reducing sugars.

SUMMARY OF THE INVENTION

The present invention is directed to a method of substantially depressing or eliminating reducing sugars present in trisodium citrate by contacting the reducing sugar with a hydroxylamine under neutral or alkaline conditions.

DETAILED DESCRIPTION OF THE INVENTION

It has been found that the presence of reducing sugars in trisodium citrate used in detergent formulations causes undesirable fading of dyes which are commonly present in commercially available laundry detergents. The present invention describes a method for depressing or eliminating such reducing sugars.

After purification of the citric acid, the acid is converted into trisodium citrate by adjusting the pH to a range of about 7 to 10 by the addition of a sodium salt, e.g., NaOH; a preferred range is from about 9 to 10.

An analysis of citric acid produced by submerged culture fermentation indicates that reducing sugars may be present in amounts ranging from less than about 0.1 to 0.25 weight of 50 percent citric acid solution. Based on this range of reducing sugars, an amount of from 0.05 to 0.09 percent by weight of hydroxylamine based on the weight of anhydrous trisodium citrate has been found to be effective in the present invention. About 0.07 to 0.09 percent by weight of hydroxylamine sulfate is preferred; about 0.05 to 0.07 percent by weight hydroxylamine chloride is preferred. For each 0.25 weight percent increase in the amount of reducing sugars present, based on 50 percent citric acid an increase of from 0.05 to 0.09 percent by weight of hydroxylamine is required to substantially depress or eliminate reducing sugars. Hydroxylamine sulfate is available in amounts for commercial processes and is a preferred hydroxylamine for use in the present invention. Hydroxylamines are soluble in aqueous citric acid solutions and remain relatively stable. The hydroxylamine can therefore be added to the citric acid solution and will remain stable until the citric acid is converted into the trisodium citrate salt by addition of NaOH.

Hydroxylamines are convenient and safe to use, with no apparent toxic or ecological problems. Excess hydroxylamines present in the citrate salt solution are converted into nitrogen and water; the hydroxylamine reacts with the carbonyl groups to form oximes. These oximes are relatively stable and have been determined not to effect the performance of the trisodium citrate as a detergent builder.

Two series of citric acid samples were prepared by submerged culture. The samples were determined to contain from about 0.10 to 0.25 percent by weight reducing sugars (based on 50 percent citric solution). Reduction or elimination of reducing sugars was achieved by adding hydroxylamine hydrochloride or hydroxylamine sulfate, and measuring the color fading of commercially available laundry detergents, as described below.

EXAMPLE 1

Aqueous citric acid samples, approximately 50 percent by weight/weight, were converted to trisodium citrate salt by adjusting the pH to about 9-10 by the addition of 50 percent NaOH (weight/weight). Varying amounts of hydroxylamine hydrochloride were added and the samples maintained at 60° C. for 12 hours. A 7 ml portion of each sample was added to 50 ml of a commercially-available laundry detergent containing a blue dye and the mixture maintained at 75° C. for 48 hours. Maintaining the mixture for this time-temperature is considered the equivalent of room temperature storage of from one to two years. The degree of fading of the blue color was determined by visual inspection, and measured against a control sample of the laundry detergent alone. The results obtained are summarized in Table I below.

TABLE I

| Sample No. | Hydroxylamine hydrochloride added* | Degree of Fading Order of Discoloration | Color |
|---|---|---|---|
| **Control A | 0 | none | Blue |
| 1 | 0 | most | Gray/Blue |
| 2 | $1.2 \times 10^{-2}$ | ↓ | Gray/Blue |
| 3 | $2.4 \times 10^{-2}$ | ↓ | Gray/Blue |
| 4 | $4.8 \times 10^{-2}$ | ↓ | Gray/Blue |
| 5 | $7.2 \times 10^{-2}$ | least | Blue |
| 6 | $9.6 \times 10^{-2}$ | same as Control A | Blue |
| 7 | $12.0 \times 10^{-2}$ | same as Control A | Blue |

*Percent by weight, based on anhydrous trisodium citrate.
**Control A consisted of 50 ml portion of commercially-available detergent, with no sodium citrate added.

The above data shows that the greatest amount of discoloration or fading of the blue detergent color was obtained when no hydroxylamine hydrochloride was added to the detergent, in the presence of the reducing-sugar containing citrate salt. Control A sample demonstrates that the detergent color does not fade in the absence of the addition of the citrate salt. As the amount of hydroxylamine hydrochloride added was increased from 0.01 percent by weight to about 0.05 to 0.09 percent by weight, the degree of color fading was progressively lowered. At about 0.05 percent by weight, the degree of color fading was acceptable. At about 0.07 to 0.09 percent by weight the color fading was substantially eliminated.

EXAMPLE II

The procedure described in Example 1 was repeated, except that hydroxylamine sulfate was used in place of hydroxylamine chloride. The results obtained are summarized below.

TABLE II

| Sample No. | Hydroxylamine sulfate added* | Degree of Fading | |
|---|---|---|---|
| | | Order of Discoloration | Color |
| **Control A | 0 | none | Blue |
| 1 | 0 | most | Gray/Blue |
| 2 | $1.2 \times 10^{-2}$ | ↓ | Gray/Blue |
| 3 | $2.4 \times 10^{-2}$ | ↓ | Gray/Blue |
| 4 | $4.8 \times 10^{-2}$ | ↓ | Gray/Blue |
| 5 | $7.2 \times 10^{-2}$ | ↓ | Gray/Blue |
| 6 | $9.6 \times 10^{-2}$ | least | Gray/Blue |
| 7 | $12.0 \times 10^{-2}$ | | Blue |

*Percent by weight, based on anhydrous trisodium citrate.
**Control A consisted of 50 ml portion of commercially-available detergent, with no sodium citrate added.

The data presented in Table II indicated that hydroxylamine sulfate is effective in eliminating reducing sugars present in the citrate, as indicated by the elimination of color fading of the detergent dye.

In order to demonstrate that the detergent dye fading was caused by the presence of reducing sugars in the trisodium citrate, the following experiment was carried out.

EXAMPLE III

Fifty gram portions of substantially pure trisodium citrate containing less than 0.1 percent reducing sugars, were mixed with 0.6 percent glucose (based on anhydrous trisodium citrate). Two series of samples were prepared; in one series varying amounts of hydroxylamine chloride were added to the trisodium citrate and glucose. In a second series, varying amounts of hydroxylamine sulfate were added. The mixtures were maintained at 60° C. for 12 hours. A 7 ml portion of each sample was added to 50 ml of a commercially available laundry detergent containing a blue dye and the mixture maintained at 75° C. for 48 hours. A control sample of the substantially pure trisodium citrate and detergent was also prepared. The degree of fading of the blue color was determined by visual inspection, and measured against the control sample containing commercially available detergent with no glucose added.

The results obtained are summarized in Table III below.

TABLE III

| Sample No. | Hydroxylamine added* | Degree of Fading | |
|---|---|---|---|
| | | Order of Discoloration | Color |
| **Control A | 0 | none | Blue |
| | Hydroxylamine Chloride | | |
| 1 | 0 | most | Gray/Blue |
| 2 | $6.0 \times 10^{-2}$ | ↓ | Gray/Blue |
| 3 | $12.0 \times 10^{-2}$ | Same as Control A | Blue |
| | Hydroxylamine Sulfate | | |
| 4 | 0 | most | Gray/Blue |
| 5 | $6.0 \times 10^{-2}$ | ↓ | Gray/Blue |
| 6 | $12.0 \times 10^{-2}$ | least | Gray/Blue |

*Percent by weight, based on anhydrous trisodium citrate.
**Control A sample consisted of a 7 ml portion of crystalline trisodium citrate mixed together with 50 ml of laundry detergent.

The data presented in Table III indicates that samples of trisodium citrate which contain glucose and no hydroxylamine showed the greatest amount of discoloration or fading of the blue detergent color. Addition of from 0.06 to 0.12 percent by weight of hydroxylamine chloride or sulfate substantially decreased or eliminated the color fading.

Highly purified trisodium citrate, which contains substantially no reducing sugars, did not cause fading of the detergent dye in Control A sample, indicating that fading of the detergent dye is due to the presence of reducing sugars, e.g., glucose, and that hydroxylamine depresses or eliminates this color fading.

As indicated earlier, from about 0.1 to 0.25 percent of reducing sugars may be present in citric acid, and that based on this range, from 0.05 to 0.09 percent by weight of hydroxylamine calculated on a volume basis of a 50 percent citric acid solution, are required to eliminate or reduce the sugars present in trisodium citrate. In order to provide a quick determination of the amount of sugar present, especially glucose, the following determination was carried out. Because the major reducing sugar present was determined to be glucose, a glucose-determining procedure was used.

Samples of sodium citrate, prepared as described in Example 1 were converted to trisodium citrate; hydroxylamine sulfate and commercial laundry detergent added as in Example 1; and the "degree of fading" measured. The amount of glucose present in the samples was determined by testing the trisodium citrate samples with reagent strips sensitive to glucose. Such reagent strips are commercially available from Ames Company, a division of Miles Laboratories, Inc., under the trade designation CLINISTIX. Results indicated that there was a correlation between the degree of fading and the amount of glucose present, as indicated by the reagent test strip. Other techniques can be used to determine the amount of reducing sugars present to calculate the amount of hydroxylamine required for use in the present invention [See Starch/Stärke 32, No. 5, pp. 174–175 (1980)].

What is claimed is:

1. A method of eliminating or substantially depressing reducing sugars present in trisodium citrate obtained from citric acid produced from a carbohydrate substrate which comprises the steps of contacting said trisodium citrate under neutral or acid conditions with from 0.05 to 0.09 percent by weight of hydroxylamine sulfate or hydroxylamine chloride based on the weight of anhydrous trisodium citrate, for each 0.25 weight percent of reducing sugars present.

2. A method as claimed in claim 1 wherein from 0.07 to 0.09 percent by weight of hydroxylamine sulfate is present.

3. A method as claimed in claim 1 wherein from 0.05 to 0.07 percent by weight of hydroxylamine chloride is present.

4. A method of eliminating or substantially depressing reducing sugars present in trisodium citrate obtained from citric acid produced from a carbohydrate substrate which comprises the steps of reducing the citric acid pH to about 7 to 10 with a sodium salt to produce trisodium citrate, and contacting said trisodium citrate under neutral or acid conditions with from about 0.07 to 0.09 percent by weight of hydroxylamine sulfate based on the weight of anhydrous trisodium citrate for each 0.25 percent of reducing sugars present.

* * * * *